United States Patent
McOsker

(10) Patent No.: US 6,329,354 B1
(45) Date of Patent: *Dec. 11, 2001

(54) METHODS FOR THE TREATMENT OF OSTEOPOROSIS

(75) Inventor: Jocelyn Elaine McOsker, Norwich, NY (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/008,859

(22) Filed: Jan. 25, 1993

Related U.S. Application Data

(63) Continuation of application No. 07/661,777, filed on Feb. 26, 1991, now abandoned.

(51) Int. Cl.⁷ .................. A61K 31/66; A61K 31/675; A61K 31/57; A61K 31/56
(52) U.S. Cl. ............... 514/109; 514/79; 514/80; 514/86; 514/167; 514/170; 514/182
(58) Field of Search ................. 514/79, 80, 86, 514/105, 107, 120, 182

(56) References Cited

U.S. PATENT DOCUMENTS

| | | | |
|---|---|---|---|
| 3,553,314 | 1/1971 | Francis | 424/49 |
| 3,683,080 | 8/1972 | Francis | 424/204 |
| 4,761,406 | 8/1988 | Flora et al. | 514/86 |

FOREIGN PATENT DOCUMENTS

| | | |
|---|---|---|
| 298553 | 1/1989 | (EP) . |
| 088462 | 9/1989 | (EP) . |

OTHER PUBLICATIONS

N. Watts et al., "Intermittent Cyclical Etidronate Treatment of Postmenopausal Osteoporosis," 323 *New England Journal of Medicine* 73 (1990).

T. Storm., "Effect of Intermittent Cyclical Etidronate Therapy on Bone Mass and Fracture Rate in Women with Postmenopausal Osteoporosis," 322 *New England Journal of Medicine* 1265 (1990).

M. Meschia et al., "Clinical Trial on Efficacy of a Combination of Elcatonin (carbocalcitonin) and conjugated Oestrogen in the Prophylaxis of Bone Mass in Normal Postmenopausal Women," 10 International Conferenceof Calcium Regulating Hormones and 11th Annual Meeting of the American Society for Bone and Mineral Research in Montreal, Canada, Sep. 9–14, 1999.

T. Wronski et al.,, "Endocrine and Pharmacological Suppressors of Bone Turnover Pocket Against Osteopenia in Ovariectomized Rats, " 125 *Endocrinology* 810 (1989).

L. Mallette et al., "Cyclic Therapy of Osteoporosis: Use of a Brief, High–Dose Pulse of Etidronate as a Terminator of Osteoclast Activity," 2 *Osteoporosis* 944 (1987).

B. Ettinger et al., "Postmenopausal Bone Loss is Prevented by Treatment with Low–Dosage Estrogen with Calcium," 106 *Annals of Internal Medicine* 40 (1987).

R. L. Lindsay, Panel Session: Prevention/Treatment, "Alternative Strategies for Prevention of Postmenopausal Osteoporosis," pp. 66–70 (1987).

R. Lindsay et al., "Osteoporosis Current Concepts," 61 *Bull. N.Y. Acad. Med.* 307 (May 1985).

C. Chestnut III, "Synthetic Salmon Calcitonin, Disphosphonates, and Anabolic Steroids in the Treatment of Postmenopausal Osteoporosis,"2 *Osteoporous* 549 (1984).

R. Lindsay et al., "the Minimum Effective Dose of Estrogen for Prevention of Postmenopausal Bone Loss," 63 *Journal of hte American College of Obstetricians and Gynecologists,* 759 (Jun. 1984).

M. Francis et al., "Chemical, Biochemical and Medicinal Properties of Disphosphonates," *The Role of Phosphonates in Living Systems,* Ch. 4, p. 55 (1983).

*Primary Examiner*—Theodore J. Criares
(74) *Attorney, Agent, or Firm*—Carl J. Roof; Brahm Corstanje; David Suter

(57) ABSTRACT

Methods of treatment for osteoporosis in a human or other animal subject, comprising: administering a bone-active phosphonate to said subject, at a level of at least about 0.1 LED per day of said treatment; and administering an estrogen hormone to said subject at a level of from about 0.2 to about 0.8 LED per day of said treatment. The bone-active phosphonate is preferably a bisphosphonate, or a phosphonoalkyl phosphonate.

17 Claims, No Drawings

METHODS FOR THE TREATMENT OF OSTEOPOROSIS

This is a continuation of application Ser. No. 07/661,777, filed on Feb. 26, 1991, now abandoned.

BACKGROUND OF THE INVENTION

This invention relates to methods of building bone in humans and other animals, i.e., for the treatment of osteoporosis and related disorders. In particular, this invention relates to such methods of treatment by administration of bone-active phosphonates and estrogen.

The most common metabolic bone disorder is osteoporosis. Osteoporosis can be generally defined as the reduction in the quantity of bone, or the atrophy of skeletal tissue. In general, there are two types of osteoporosis: primary and secondary. "Secondary osteoporosis" is the result of an identifiable disease process or agent. However, approximately 90% of all osteoporosis cases is idiopathic "primary osteoporosis". Such primary osteoporosis includes post-menopausal osteoporosis, age-associated osteoporosis (affecting a majority of individuals over the age of 70 to 80), and idiopathic osteoporosis affecting middle-aged and younger men and women.

For some osteoporotic individuals the loss of bone tissue is sufficiently great so as to cause mechanical failure of the bone structure. Bone fractures often occur, for example, in the hip and spine of women suffering from postmenopausal osteoporosis. Kyphosis (abnormally increased curvature of the thoracic spine) may also result.

The mechanism of bone loss in osteoporotics is believed to involve an imbalance in the process of "bone remodeling". Bone remodeling occurs throughout life, renewing the skeleton and maintaining the strength of bone. This remodeling involves the erosion and filling of discrete sites on the surface of bones, by an organized group of cells called "basic multicellular units" or "BMUs". BMUs primarily consist of "osteoclasts", "osteoblasts", and their cellular precursors. In the remodeling cycle, bone is resorbed at the site of an "activated" BMU by an osteoclast, forming a resorption cavity. This cavity is then filled with bone by an osteoblast.

Normally, in adults, the remodeling cycle results in a small deficit in bone, due to incomplete filling of the resorption cavity. Thus, even in healthy adults, age-related bone loss occurs. However, in osteoporotics, there is an increase in the number of BMUs that are activated. This increased activation accelerates bone remodeling, resulting in abnormally high bone loss.

Although its etiology is not fully understood, there are many risk factors thought to be associated with osteoporosis. These include low body weight, low calcium intake, physical inactivity, and estrogen deficiency.

Many compositions and methods are described in the medical literature for the "treatment" of osteoporosis. Many of these compositions and methods attempt to either slow the loss of bone or to produce a net gain in bone mass. See, for example, R. C. Haynes, Jr. et al., "Agents affecting Calcification", *The Pharmacological Basis of Therapeutics*, 7th Edition (A. G. Gilman, L. S. Goodman et al., Editors, 1985); G. D. Whedon et al., "An Analysis of Current Concepts and Research Interest in Osteoporosis", *Current Advances in Skeletogenesis* (A. Ornoy et al., Editors, 1985); and W. A. Peck, et al., *Physician's Resource Manual on Osteoporosis* (1987), published by the National Osteoporosis Foundation.

Among the treatments for osteoporosis suggested in the literature is the administration of bisphosphonates or other bone-active phosphonates. See, for example, Storm et al., "Effect of Intermittent Cyclical Etidronate Therapy on Bone Mineralization and Fracture Rate in Women with Post-Menopausal Osteoporosis", 322 *New England Journal of Medicine* 1265 (1990); and Watts et al., "Intermittent Cyclical Etidronate Treatment of Post-Menopausal Osteoporosis", 323 *New England Journal of Medicine* 73 (1990). Such treatments using a variety of bisphosphonates are described in U.S. Pat. No. 4,761,406, Flora et al., issued Aug. 2, 1988; U.S. Pat. No. 4,812,304, Anderson et al., issued Mar. 14, 1989; U.S. Pat. No. 4,812,311, Uchtman, issued Mar. 14, 1989; and U.S. Pat. No. 4,822,609, Flora, issued Apr. 18, 1989. The use of such phosphonates for the treatment of osteoporosis, and other disorders involving abnormal calcium and phosphate metabolism, is also described in U.S. Pat. No. 3,683,080, Francis, issued Aug. 8, 1972; U.S. Pat. No. 4,330,537, Francis, issued Oct. 28, 1980; U.S. Pat. No. 4,267,108, Blum et al., issued May 12, 1981; European Patent Publication 298,553, Ebetino, published Jan. 11, 1989; and Francis et al., "Chemical, Biochemical, and Medicinal Properties of the Diphosphonates", *The Role of Phosphonates in Living Systems* 55 (1983).

Administration of estrogen is also used as a means to prevent osteoporosis in postmenopausal women. This therapy typically involves daily administration of from about 0.625 milligrams to about 1.25 milligrams of conjugated estrogens, or equivalent amounts of other estrogen hormones. Estrogen may also be used to treat osteoporosis (i.e., actual building of bone in osteoporotics), although this has not been fully established. See, for example, Barzel, "Estrogens in the Prevention and Treatment of Post-Menopausal Osteoporosis: a Review", 85 *American Journal of Medicine* 847 (1988); Barzel, "Estrogen Therapy for Osteoporosis: Is it Effective?", *Hospital Practice* 95 (1990); Ettinger, et al., "Post-Menopausal Bone Loss is Prevented by Treatment with Low-Dosage Estrogen with Calcium", 106 *Annals in Internal Medicine* 40 (1987); Lindsay, et al., "The Minimum Effective Dose of Estrogen for Prevention of Post-Menopausal Bone Loss", 63 *Obstetrics and Gynecology* 759 (1984); and "Estrogen", *Drug Information* 1765 (1990). Furthermore, the use of estrogen has been associated with certain side effects, such as uterine bleeding. See, Rudy, "Hormone Replacement Therapy—How to Select the Best Preparation and Regimen," 88 *Postgraduate Medicine* 157 (1990).

Applicant has found, surprisingly, that osteoporosis may be prevented or treated by administering bone-active phosphonates with low, otherwise ineffective, doses of estrogen. Further, these methods also allow the use of low, otherwise marginally or ineffective, doses of the phosphonates. Accordingly, the methods of this invention provide effective methods of preventing and treating osteoporosis, with reduced side effects compared to such methods known in the art.

SUMMARY OF THE INVENTION

The present invention provides methods of treatment for osteoporosis in a human or other animal subject, comprising: administering a bone-active phosphonate to said subject, at a level of at least about 0.1 LED per day of said treatment; and administering an estrogen hormone to said subject at a level of from about 0.2 to about 0.8 LED per day of said treatment. The bone-active phosphonate is preferably a bisphosphonate, or a phosphonoalkyl phosphonate.

DESCRIPTION OF THE INVENTION

The methods of the present invention comprise the administration of bone-active phosphonates and estrogen hormones to a human or other animal subject. Specific compounds and compositions to be used in these processes must, accordingly, be pharmaceutically-acceptable. As used herein, such a "pharmaceutically-acceptable" component is one that is suitable for use with humans and/or animals without undue adverse side effects (such as toxicity, irritation, and allergic response) commensurate with a reasonable benefit/risk ratio. Further, as used herein, the term "safe and effective amount" refers to the quantity of a component which is sufficient to yield a desired therapeutic response without undue adverse side effects (such as toxicity, irritation, or allergic response) commensurate with a reasonable benefit/risk ratio when used in the manner of this invention. The specific "safe and effective amount" will, obviously, vary with such factors as the particular condition being treated, the physical condition of the patient, the duration of the treatment, the nature of concurrent therapy (if any), and the specific formulations employed.

Active Materials
Bone-Active Phosphonates:

The methods of this invention involve the administration of a bone-active phosphonate. As referred to herein, a "bone-active phosphonate" includes one or more compounds of the general formula

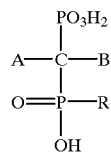

(1)

and pharmaceutically-acceptable salts and esters thereof, wherein A, B, and R are as defined hereinafter.

In Formula (1), "R" is hydroxy (for bisphosphonates), or hydrogen or alkyl (for phosphonoalkyl phosphinates). In the phosphonoalkyl phosphinates, R is preferably unsubstituted alkyl, especially lower alkyl. When R is substituted alkyl, preferred substituents include halogen, unsubstituted or substituted phenyl, unsubstituted or substituted pyridinyl, unsubstituted amino, amino substituted with one or two lower alkyl groups, hydroxy, or carboxy. More preferred substituents are fluoro, phenyl, unsubstituted amino, and hydroxy; most preferred are fluoro (especially when present as trifluoromethyl) and phenyl.

Particularly preferred R moieties in the phosphonoalkyl phosphinates are unsubstituted lower alkyl groups, especially unsubstituted, straight-chain, saturated lower alkyl groups. Also preferred R moieties are methyl, ethyl, n-propyl, iso-propyl, n-butyl, iso-butyl, sec-butyl, tert-butyl, and n-hexyl. More preferably, R is methyl, ethyl, n-propyl, or n-butyl. Most preferably, R is methyl.

In Formula (1), "A" is hydrogen; halogen; nitro; alkyl; heterocycle; aryl; heteroaryl; unsubstituted amino, or the amide thereof derived from a carboxylic acid of a substituent group; amino substituted with one substituent group, or the amide thereof derived from a carboxylic acid of a substituent group; amino substituted independently with one alkyl group and one substituent group; hydroxy, or the ester thereof derived from a carboxylic acid of a substituent group; ether having a substituent group; thiol, or the thiol ester thereof derived from a carboxylic acid of a substituent group; thioether having a substituent group, or the sulfoxide and sulfone derivative thereof; —$SO_3H$, the pharmaceutically-acceptable salts thereof, the ester thereof derived from an alcohol of a substituent group, the unsubstituted amide thereof, or the amide thereof substituted with one or two alkyl groups; —$CO_2H$, the pharmaceutically-acceptable salts thereof, the ester thereof derived from an alcohol of a substituent group, the unsubstituted amide thereof, or the amide thereof substituted with one or two alkyl groups; aldehyde; ketone having a substituent group; carbamate, unsubstituted or substituted with one or two alkyl groups; peptides having from about 1 to about 100 amino acid moieties; or the A and B moieties are covalently linked to form a ring having from 3 to 7 atoms with from 0 to 3 heteroatoms selected from the group consisting of nitrogen, sulfur, phosphorus and oxygen, the ring being unsubstituted or substituted with one or more of the above substituents of A; or the A and B moieties are replaced by an unsubstituted or substituted alkyl moiety attached to the geminal carbon (the carbon shown in structure (1) hereinabove) by a double bond.

Preferably, A is one of the following moieties.
(1) hydrogen
(2) halogen (preferably fluoro or chloro, more preferably fluoro)
(3) substituted or unsubstituted alkyl having the general structure

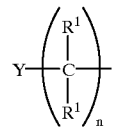

(2)

wherein:
(a) n is an integer from 1 to 10, preferably from 1 to 5, more preferably 1 or 2, more preferably 1;
(b) each $R^1$ is, independently, hydrogen, halogen, lower alkyl, unsubstituted amino or the amide thereof derived from a carboxylic acid of a lower alkyl group, amino substituted with one lower alkyl group or the amide thereof derived from a carboxylic acid of a lower alkyl group, amino substituted independently with two lower alkyl groups, hydroxy or the ester thereof derived from a carboxylic acid of a lower alkyl group, —$CO_2H$ or the pharmaceutically-acceptable salts thereof or the ester thereof derived from an alcohol of a lower alkyl group or the unsubstituted amide thereof or the amide thereof substituted with one or two lower alkyl groups, ether having a lower alkyl group, —$PO_3H_2$ or the pharmaceutically-acceptable salts thereof, and nitro, or two $R^1$'s on the same carbon atom are =O or =$NR^9$ (where $R^9$ is lower alkyl or may be hydrogen when there is another nitrogen atom attached to the same carbon atom as the =$NR^9$ moiety), or two $R^1$'s on adjacent carbon atoms may be replaced by an additional bond between the carbon atoms; or an $R^1$ on the first carbon atom (from the right side of structure (2) hereinabove) and B (see structure (1) hereinabove) may be replaced by an additional bond; and (c) Y is halogen; nitro; cyano; heterocycle; aryl; heteroaryl; unsubstituted amino, and the amide thereof derived from a carboxylic acid of an alkyl, heterocycle, aryl or heteroaryl group; amino substituted with one alkyl, heterocycle, aryl or heteroaryl group and the amide thereof derived from a carboxylic acid of an alkyl group; amino substituted independently with one alkyl group and one alkyl, heterocycle, aryl or heteroaryl group; hydroxy, and the ester thereof derived from a carboxylic acid of an alkyl, heterocycle, aryl or heteroaryl group; ether having an alkyl, heterocycle, aryl or heteroaryl group; thiol, and the thiol ester thereof derived from a carboxylic acid of an alkyl, heterocycle, aryl or heteroaryl group; thioether having an alkyl, heterocycle, aryl or heteroaryl group, and the sulfoxide and sulfone derivatives thereof; —SO$_3$H, the pharmaceutically-acceptable salts thereof, the ester thereof derived from an alcohol of an alkyl group, the unsubstituted amide thereof, and the amide thereof substituted with one or two alkyl groups; —CO$_2$H, the pharmaceutically-acceptable salts thereof, the ester thereof derived from an alcohol of an alkyl group, the unsubstituted amide thereof, and the amide thereof substituted with one or two alkyl groups; PO$_3$H$_2$, the pharmaceutically-acceptable salts thereof, the ester thereof derived from an alcohol of an alkyl group, the unsubstituted amide thereof, and the amide thereof substituted with one or two alkyl groups; —(R$^8$)PO$_2$H (where R$^8$ is hydrogen or unsubstituted lower alkyl), the pharmaceutically-acceptable salts thereof, the ester thereof derived from an alcohol of an alkyl group, the unsubstituted amide thereof, and the amide thereof substituted with one or two alkyl groups; aldehyde; ketone having an alkyl group; carbamate, unsubstituted or substituted with one or two alkyl groups; or peptidyl. For bisphosphonates, Y is preferably a heterocycle (preferably 5 to 7 membered heterocycles having one or two nitrogen atoms); amino; and substituted amino. Particularly preferred Y moieties include pyridyl, amino, and amino substituted with one or two lower alkyl groups. Preferably, for phosphonoalkyl phosphinates, Y is halogen (preferably fluoro); trifluoromethyl; ether having a lower alkyl group; unsubstituted amino, and the amide thereof derived from a carboxylic acid of a lower alkyl group, amino substituted with one lower alkyl group and the amide thereof derived from carboxylic acid of a lower alkyl group; amino substituted independently with two lower alkyl groups; or peptidyl having from one to about six amino acid moieties.

(4) cycloalkyl having from 4 to 10 carbon atoms, preferably 5 or 6 carbon atoms (5) heterocycle having S or 6 atoms in the ring; more preferably one or two nitrogen atoms in the ring, more preferably having one nitrogen atom in the ring. Particularly preferred heterocycles are unsubstituted or substituted piperidinyl, pyrrolidinyl, piperazinyl, and morpholinyl.

(6) unsubstituted and substituted phenyl and naphthyl (7) unsubstituted and substituted 5 and 6 membered ring heteroaryls having one or two heteroatoms (especially nitrogen heteroatoms), preferably pyridinyl (8) an amine-containing moiety having the general structure:

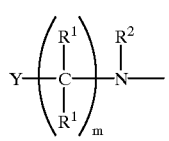

(3)

wherein
(a) m is an integer from 0 to 10, preferably from 0 to 5, more preferably 0 or 1, more preferably 0;

(b) R$^1$ and Y are as described hereinbefore; and
(c) R$^2$ is hydrogen, lower alkyl or acyl derived from a carboxylic acid of a lower alkyl (9) an oxygen-containing moiety having the general structure:

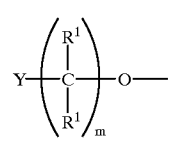

(4)

wherein
(a) m is an integer from 0 to 10, preferably from 0 to 5, more preferably 0 or 1, more preferably 0; and
(b) R$^1$ and Y are as described hereinbefore

(10) sulfur-containing moiety having the general structure:

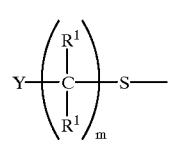

(5)

wherein
(a) m is an integer from 0 to 10, preferably from 0 to 5, more preferably 0 or 1, more preferably 0; and
(b) R$^1$ and Y are as described hereinbefore In Formula (1), "B" is hydrogen; halogen; unsubstituted or substituted lower alkyl; unsubstituted or substituted cycloalkyl having from 3 to 7 atoms in the ring; unsubstituted or substituted heterocycle having from 3 to 7 atoms in the ring; unsubstituted or substituted phenyl; hydroxy, or the ester thereof derived from a carboxylic acid of a lower alkyl group; thiol; unsubstituted amino, or the amide thereof derived from a carboxylic acid of a lower alkyl group; amino substituted with one lower alkyl group, or the amide thereof derived from a carboxylic acid of a lower alkyl group; amino substituted independently with two lower alkyl groups; or —CO$_2$H, the pharmaceutically-acceptable salts thereof, the ester thereof derived from an alcohol of a lower alkyl group, the unsubstituted amide thereof, or the amide thereof substituted with one or two lower alkyl groups.

To maintain chemical stability of these compounds, the A and B moieties preferably do not both have heteroatoms (nitrogen, oxygen or sulfur), or a heteroatom and a halogen, bonded to the phosphonate moiety (i.e., the carbon atom geminally substituted with the phosphorous atoms). Thus, when the A moiety has an oxygen, sulfur, nitrogen, or halogen atom bonded to the phosphorous-substituted methylene carbon, then B is selected from hydrogen; unsubstituted or substituted lower alkyl, cycloalkyl, heterocycle (where a carbon atom of the heterocycle is bonded to the geminal carbon atoms), or phenyl; —CO$_2$H, the pharmaceutically-acceptable salts thereof, the ester thereof derived from an alcohol of a lower alkyl group, the unsubstituted amide thereof, and the amide thereof substituted with one or two lower alkyl groups.

Preferably B is hydrogen, halogen, unsubstituted or substituted lower alkyl, unsubstituted or substituted phenyl, unsubstituted or substituted benzyl, hydroxy or the ester thereof derived from a carboxylic acid of a lower alkyl group, thiol, unsubstituted amino or the amide thereof derived from a carboxylic acid of a lower alkyl group, amino substituted with one lower alkyl group or the amide thereof derived from a carboxylic acid of a lower alkyl group, amino substituted independently with two lower alkyl groups, or —$CO_2H$ or the pharmaceutically-acceptable salts thereof and the ester thereof derived from an alcohol of a lower alkyl group and the unsubstituted amide thereof or the amide thereof substituted with one or two lower alkyl groups.

More preferably, B is hydrogen, chloro, methyl, ethyl, hydroxy, thiol, unsubstituted amino, (N-methyl)amino, (N,N-dimethyl)amino, —$CO_2H$ or the pharmaceutically-acceptable salts thereof, —$CO_2CH_3$, or —$CONH_2$. More preferably, B is hydrogen, methyl, chloro, amino, or hydroxy; more preferably hydrogen, or hydroxy, or amino, or thiol; more preferably hydroxy. Particularly preferred bone-active phosphonates include those wherein A is a moiety of groups (3) or (8) above, and B is hydroxy.

Particularly preferred bisphosphonates useful herein are of the formula:

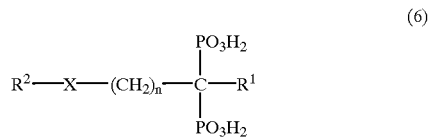 (6)

wherein: n is an integer from 0 to 7 (preferably from 0 to 2, more preferably 1); $R^1$ is hydrogen, chloro, amino, or hydroxy (preferably hydrogen or hydroxy); X is —NH—, oxygen, or a single bond (preferably —NH—or single bond); $R^2$ is a 5- to 7-membered heterocycle having from 1 to 3 heteroatoms (preferably a 6-membered heterocycle having 1 or 2 nitrogen atoms), amino, amino substituted with one or two lower alkyl groups, or hydrogen; and their pharmaceutically-acceptable salts and esters.

The term "pharmaceutically-acceptable salts and esters", as used herein, means hydrolyzable esters and salts of the bone-active phosphonates which have the same general pharmacological properties as the acid form from which they are derived, and which are pharmaceutically acceptable. Pharmaceutically-acceptable salts include, for example, alkali metals (e.g., sodium and potassium), alkaline earth metals (e.g., calcium and magnesium), non-toxic heavy metals (e.g., stannous and indium), and ammonium and low molecular weight substituted ammonium (e.g., mono-, di- and triethanolamine) salts. Preferred compounds are the sodium, potassium, and ammonium salts. Pharmaceutically-acceptable esters include unsubstituted and substituted alkyl, aryl and phosphoryl esters. Nonlimiting examples of pharmaceutically-acceptable esters include, for example, isopropyl, tertiarybutyl, 2-chloroethyl, 2,2,2-trichloroethyl, 2,2,2-trifluoroethyl, p-toluenesulfonylethyl, glycyl, sarcosyl, benzyl, phenyl, 1,2-hexanoylglyceryl, p-nitrophenyl, 2,2 dimethyl-1,3-dioxolene-4-methyl, isopentenyl, o-carbomethoxyphenyl, piraloyloxymethylsalicylyl, diethylamidophosphoryl, pivaloyloxymethyl, acyloxymethyl, propionyloxyethyl, isobutyryloxymethyl, dodecyl, octadecyl, and isopropyloxymethyl.

Specific examples and definitions for substituents useful in the compounds of Formulas (1) through (6) are described in European Patent Publication 298,553, Ebetino, published Jan. 11, 1989 (incorporated by reference herein). That application also describes phosphonoalkyl phosphinates useful in the methods of this invention (wherein R is hydrogen or alkyl), and methods for making such compounds. Methods of making phosphonoalkyl phosphinates are also described in European Patent Publication 298,555, Ebetino, published Jan. 11, 1989 (incorporated by reference herein).

Bisphosphonates useful in the methods of this invention (wherein R is hydroxy), and methods for making such compounds, are described in the following patent documents, all incorporated by reference herein: U.S. Pat. No. 3,553,314, Francis, issued Jan. 5, 1971; U.S. Pat. No. 3,683,080, Francis, issued Aug. 8, 1972; U.S. Pat. No. 3,846,420, Wollmann et al., issued Nov. 5, 1974; U.S. Pat. No. 3,899,496, Schindler et al., issued Aug. 12, 1975; U.S. Pat. No. 3,941,772, Ploger et al., issued Mar. 2, 1976; U.S. Pat. No. 3,957,160, Ploger et al., issued May 18, 1976; U.S. Pat. No. 3,962,432, Schmidt-Dunker, issued Jun. 8, 1976; U.S. Pat. No. 3,979,385, Wollmann et al., issued Sep. 7, 1976; U.S. Pat. No. 3,988,443, Ploger et al., issued Oct. 26, 1976; U.S. Pat. No. 4,054,598, Blum et al., issued Oct. 18, 1977; U.S. Pat. No. 4,113,861, Fleisch et al., issued Sep. 12, 1978; U.S. Pat. No. 4,117,090, Ploger, issued Sep. 26, 1978; U.S. Pat. No. 4,134,969, Schmidt-Dunker, issued Jan. 16, 1979; U.S. Pat. No. 4,267,108, Blum et al., issued May 12, 1981; U.S. Pat. No. 4,304,734, Jary et al., issued Dec. 8, 1981; U.S. Pat. No. 4,330,537, Francis, issued May 18, 1982; U.S. Pat. No. 4,407,761, Blum et al., issued Oct. 4, 1983; U.S. Pat. No. 4,469,686, Andrews, issued Sep. 4, 1984; U.S. Pat. No. 4,578,376, Rosini, issued Mar. 25, 1986; U.S. Pat. No. 4,608,368, Blum et al., issued Aug. 26, 1986; U.S. Pat. No. 4,621,077, Rosini et al., issued Nov. 4, 1986; U.S. Pat. No. 4,687,767, Bosies et al., issued Aug. 18, 1987; U.S. Pat. No. 4,687,768, Benedict et al., issued Oct. 18, 1987; U.S. Pat. No. 4,711,880, Stahl et al., issued Dec. 8, 1987; U.S. Pat. No. 4,719,203, Bosies et al., issued Jan. 12, 1988; U.S. Pat. No. 4,927,814, Gall et al., issued May 22, 1990; U.S. Pat. No. 4,990,503, Isomura et al., issued Feb. 5, 1991; German Offenlegungsschrift 2,104,476, Worms, published Aug. 17, 1972; German Offenlegungsschrift 2,343,147, Ploeger et al., published Apr. 3, 1975; German Offenlegungsschrift 2,360,798, Worms et al., published Jun. 26, 1975; German Offenlegungsschrift 2,513,966, Schmidt-Dunker, published Oct. 7, 1976; German Offenlegungsschrift 2,541,981, Eimers et al., published Mar. 24, 1977; German Offenlegungsschrift 3,334,211, Blum, published Apr. 4, 1985; Japanese Patent Publication 78/59,674, Suzuki et al., published May 29, 1978; Japanese Patent Publication 79/135,724, Suzuki et al., published Oct. 22, 1979; Japanese Patent Publication 80/98193, Suzuki et al., published Jul. 25, 1980; European Patent Publication 88,359, Blum et al., published Sep. 14, 1983; European Patent Publication 100,718, Breliere et al., published Feb. 15, 1984; European Patent Publication 186,405, Benedict et al., published Jul. 2, 1986; European Patent Publication 197,478, Bosies et al., published Oct. 15, 1986; European Patent Publication 230,068, Benedict et al., published Jul. 29, 1987; European Patent Publication 273,514, Ebetino et al., published Jul. 6, 1988; European Patent Publication 274,158, Ebetino et al., published Jul. 13, 1988; European Patent Publication 282,309, Sakamoto et al., published Sep. 14, 1988; European Patent Publication 282,320, Isomura et al., published Sep. 14, 1988; PCT Patent Publication 87/03598, Binderup et al., published Jun. 18, 1987; and PCT Patent Publication 88/00590, Gall et al., published Jan. 28, 1988.

Preferred bone-active phosphonates useful in the methods of this invention include: N-(2'-(3'-methyl)-pyridinyl) aminomethane phosphonomethylphosphinic acid; N-(2'-(5'-methyl)-pyridinyl)amino methane phosphonomethylphosphinic acid; N-(2'-(3'-methyl)-piperidinylidene) aminomethane phosphonomethylphosphinic acid; N-(2'-(5'-methyl)-piperidinylidene)aminomethane phosphonomethylphosphinic acid; 2-(2'-pyridinyl)ethane-1-phosphono-1-methylphosphinic acid; 2-(2'-piperidinyl)

ethane-1-phosphono-1-methylphosphinic acid; 2-(p-aminophenyl)-1-hydroxy-ethane-1-phosphono-1-methylphosphinic acid; 2-(m-aminophenyl)-1-hydroxyethane-1-phosphono-1-methylphosphinic acid; N-(1-(5-amino-2-methyl-1-oxo)-pentyl)aminomethane phosphonomethylphosphinic acid; N-(2'-(3'-methyl)-piperidinylidene)aminomethane phosphonobutylphosphinic acid; S-(2'-pyridinyl)thiomethane phosphonomethylphosphinic acid; 2-(2-pyridyl)-1-hydroxyethane-1-phosphono-1-methyl phosphinic acid; 2-(3-pyridyl)-1-hydroxyethane-1-phosphono-1-methylphosphinic acid; 2-(N-imidazoyl)-1-hydroxyethane-1-phosphono-1-methylphosphinic acid; 3-(N-pentyl-N-methylamino)-1-hydroxypropane-1-phosphono-1-methylphosphinic acid; 4-amino-1-hydroxybutane-1-phosphono-1-methylphosphinic acid; 3-(N-pyrollidino)-1-hydroxypropane-1-phosphono-1-methylphosphinic acid; N-cycloheptyl aminomethane-phosphonomethylphosphinic acid; S-(p-chlorophenyl) thiomethanephosphonomethylphosphinic acid; (7-dihydro-1pyrindine)methanephosphonomethylphosphinic acid; (7-dihydro-1-pyrindine) hydroxymethanephosphonomethylphosphinic acid; (6-dihydro-2-pyrindine) hydroxymethanephosphonomethylphosphinic acid; 2-(6-pyrolopyridine)-1-hydroxyethane-1-phosphono-1-methyl phosphinic acid; 1-hydroxyethane-1,1-bisphosphonic acid; 1-hydroxy pentane-1,1-bisphosphonic acid; methane bisphosphonic acid; dichloromethanebisphosphonic acid; hydroxymethanebisphosphonic acid; 1-aminoethane-1,1-bisphosphonic acid; 2-aminoethane-1,1-bisphosphonic acid; 3-aminopropane-1,1-bisphosphonic acid; 3-aminopropane-1-hydroxy-1,1-bisphosphonic acid; 3-(dimethylamino)-1-hydroxypropane-1,1-bisphosphonic acid; 3,3-dimethyl-3-amino-1-hydroxypropane-1,1-bisphosphonic acid; phenylaminomethane bisphosphonic acid; N,N-dimethylaminomethane bisphosphonic acid; N-(2-hydroxyethyl) aminomethane-bisphosphonic acid; 4-amino-1-hydroxybutane-1,1-bisphosphonic acid; 5-amino-1-hydroxypentane-1,1-bisphosphonic acid; 6-amino-1-hydroxyhexane-1,1-bisphosphonic acid; indan-2,2-bisphosphonic acid; hexahydroindan- 2,2-bisphosphonic acid; 2-methylcyclobutane-1,1-bisphosphonic acid; 3-chlorocyclopentane-1,1-bisphosphonic acid; cyclohexane-1,1-bisphosphonic acid; 2-(2-pyridyl)-1-hydroxyethane-1,1-bisphosphonic acid; N-(2-(5-amino)-pyridyl)-aminomethane bisphosphonic acid; N-(2-(5-chloro)-pyridyl)-aminomethane bisphosphonic acid; N-(2-(3-picolyl))-aminomethane bisphosphonic acid; N-(2-(4-picolyl))-aminomethane bisphosphonic acid; N-(2-(5-picolyl))-aminomethane bisphosphonic acid; N-(2-(6-picolyl))-aminomethane bisphosphonic acid; N-(2-(3,4-lutidine))-aminomethane bisphosphonic acid; N-(2-pyrimidyl)-aminomethane bisphosphonic acid; N-(2-pyridyl)-2-aminoethane-1,1-bisphosphonic acid; 2-(2-pyridyl)-ethane-1,1-bisphosphonic acid; 2-(3-pyridyl)-ethane-1,1-bisphosphonic acid; 2-(4-pyridyl)-ethane-1,1-bisphosphonic acid; 2-(2-(3-picolyl))-oxaethane-1,1-bisphosphonic acid; 2-(3-pyridyl)-1-hydroxyethane-1,1-bisphosphonic acid; 2-(N-imidazoyl)-1-hydroxyethane-1,1-bisphosphonic acid; 3-(N-pentyl-N-methylamino)-1-hydroxypropane-1,1-bisphosphonic acid; 3-(N-pyrollidino)-1-hydroxypropane-1,1-bisphosphonic acid; N-cycloheptylaminomethane bisphosphonic acid; S-(p-chlorophenyl) thiomethanebisphosphonic acid; (7-dihydro-1-pyrindine)methanebisphosphonic acid; (7-dihydro-1-pyrindine)hydroxymethanebisphosphonic acid; (6-dihydro-2-pyrindine)hydroxymethanebisphosphonic acid; 2-(6-pyrolopyridine)-1-hydroxyethane-1,1-bisphosphonic acid; and pharmaceutically-acceptable salts and esters thereof.

Particularly, preferred bone-active phosphonates useful in the methods of this invention include: 1-hydroxyethane-1, 1-bisphosphonic acid; dichloromethane bisphosphonic acid; 3-amino-1-hydroxypropane-1,1-bisphosphonic acid; 6-amino-1-hydroxyhexane-1,1-bisphosphonic acid; 4-amino-1-hydroxybutane-1,1-bisphosphonic acid; 2-(3-pyridyl)-1-hydroxyethane-1,1-bisphosphonic acid; 2-(N-imidazoyl)-1-hydroxyethane-1,1-bisphosphonic acid; 3-(N-pentyl-N-methylamino)-1-hydroxypropane-1,1-bisphosphonic acid; 3-(N-pyrollidino)-1-hydroxypropane-1, 1-bisphosphonic acid; N-cycloheptylaminomethanebisphosphonic acid; S-(p-chlorophenyl) thiomethanebisphosphonic acid; (7-dihydro-1-pyrindine)methane bisphosphonic acid; (7-dihydro-1-pyrindine)hydroxymethane bisphosphonic acid; (6-dihydro-2-pyrindine)hydroxymethanebisphosphonic acid; 2-(6-pyrolopyridine)-1-hydroxyethane-1,1-bisphosphonic acid; and pharmaceutically-acceptable salts and esters thereof.

Estrogen Hormone:

The methods of this invention also involve administration of an estrogen hormone. As referred to herein, an "estrogen hormone" refers to naturally occurring hormones, synthetic steroidal compounds, and non-steroidal compounds, and conjugates, metabolites and derivatives thereof, which having estrogenic activity. Naturally-occurring estrogen hormones are steroids which contain a cyclopentanoperhydrophenathrene ring system. Such naturally-occurring estrogen hormones are obtained from pregnant mares' urine or prepared synthetically, using methods well-known in the art. See: "Estrogens", *Drug Information* 1765 (1990); and Rudy, "Hormone Replacement Therapy—How to Select the Best Preparation and Regimen," 88 *Postgraduate Medicine* 157 (1990); and C. Christiansen et al., "Estrogens, Bone Loss and Prevention," 1 *Osteoporosis Int.* 7 (1990); all of which are incorporated by reference herein.

Estrogen hormones useful in the methods of this invention include, for example, estradiol, estrone, estriol, equilin, equilenin, estradiol cypionate, estradiol valerate, ethinyl estradiol, polyestradiol phosphate, estropipate, diethylstilbestrol, dienestrol, chlorotrianisene, and mixtures thereof. A preferred estrogen hormone useful herein is "conjugated estrogen", which is a mixture of sodium salts of the water-soluble sulfate esters of estrone and equilin. Such conjugated estrogens may also contain other estrogenic substances found in pregnant mares' urine, such as 17-α-dihydroequiline, 17-α-estradiol, equilenin, and 17-α-dihydroequilenin.

Methods of Treatment

This invention provides methods for treating osteoporosis in a human or other animal subject, comprising: administering a bone-active phosphonate to said subject at a level of at least about 0.1 LED per day of said treatment; and administering an estrogen hormone to said subject from about 0.2 to about 0.8 LED per day of said treatment. Preferably the method comprises administering from about 0.1 to about 2 LED of the bone-active phosphonate. A particularly preferred method comprises administering from about 0.1 LED to about 0.9 LED of the phosphonate. Preferably from about 0.3 to about 0.6 LED of the estrogen hormone is administered.

As used herein, the term "LEO", or "least effective dose", is the minimum dose of active which is effective, by itself, to cause a significant inhibition of bone resorption. (As used herein, the term "active" refers to either the bone-active phosphonate, the estrogen hormone, or both.) As with any pharmaceutically-active material, the specific LEDs of the actives will vary depending upon their chemical composition, and their method of administration (i.e., oral or parenteral). Nevertheless, the LED for specific actives useful herein may be determined using methods well known in the art.

In particular, the LEDs for the bone-active phosphonates may be determined using any of several art-recognized in vivo models. One such model is the thyroparathyroidectomized ("TPTX") rat model. In this model, compounds are evaluated for in vivo bone resorption inhibition potency, by measuring their ability to inhibit the increase of serum calcium levels caused by administration of parathyroid hormone in rats whose parathyroid gland has been removed. This model is described in Russell et al., 6 *Calcified Tissue Research* 183 (1970); Muhlbauer et al., 5 *Mineral Electrolite Metabolism* 296 (1981); U.S. Pat. No. 4,761,406, Flora et al., issued Aug. 2, 1988; and European Patent Publication 298,553, Ebetino, published Jan. 11, 1989; all of which are incorporated by reference herein.

Another model is the "Schenk Model", which measures the effects of bone active phosphonates on bone growth in young rats. This model is described in Schenk et al., 11, *Calcif. Tissue Res.* 196 (1973); Shinoda et al., 35 *Calcif. Tissue Int.* 87 (1983); U.S. Pat. No. 4,761,406, Flora et al., issued Aug. 2, 1988; and European Patent Publication 298, 553, Ebetino, published Jan. 11, 1989; all of which are incorporated by reference herein.

Another model is the "ovariectomized" or "OVX" rat model, which measures the ability of bone active phosphonates to prevent loss of bone in female rates induced by ovariectomy. This model is described in Wronski et al., 125 *Endocrinology* 810 (1989), incorporated by reference herein.

The LEDs for parenteral dosing of preferred bone-active phosphonates useful herein are: 1.0 mg P/kg, for 1-hydroxyethane-1,1-bisphosphonic acid; 0.5 mg P/kg, for dichloromethane bisphosphonic acid; 0.03 mg P/kg, for 3-amino-1-hydroxypropane-1,1-bisphosphonic acid; 0.001 mg P/kg, for 4-amino-1-hydroxybutane-1,1-bisphosphonic acid; 0.1 mg P/kg, for 6-amino-1-hydroxyhexane-1,1-bisphosphonic acid; 0.01 mg P/kg, for N-(2-pyridyl) aminomethane-1,1-bisphosphonic acid; 0.0003 mg P/kg, for 2-(3-pyridyl)-1-hydroxyethane-1,1-bisphosphonic acid; 0.0001 mg P/kg, for N-cycloheptyl-aminomethanebisphosphonic acid; 0.0001 mg P/kg, for 3-(N-pentyl-N-methylamino)-1-hydroxypropane-1,1-bisphosphonic acid; 0.01 mg P/kg, for 3-(dimethylamino)-1-hydroxypropane-1,1-bisphosphonic acid; 0.01 mg P/kg, for 3-(N-pyrollidino)-1-hydroxypropane-1,1-bisphosphonic acid; 0.03 mg P/kg, for N-cycloheptylaminomethanebisphosphonic acid; and 0.3 mg P/kg for S-(p-chlorophenyl)thiomethanebisphosphonic acid. (The LEDs for oral dosing would be higher, depending upon the systemic absorption of the phosphonate. Typically, absorption from oral administration is from about 1% to about 10%. Thus, oral LEDs are typically about ten- to one hundred-fold higher than the parenteral LEDs.)

As used herein, the term "mg P/kg" refers to the amount of compound, expressed as milligrams phosphorus in the compound, per kilogram weight of the subject to be treated. Expression of the amount of compound in terms of its phosphorus content ("mg P") is done to standardize the amount of the phosphonates to be used in the pharmaceutical compositions and methods of the present invention. For example, 2-(2'-piperidinyl)-ethane-1-phosphono-1-methylphosphinic acid has a molecular weight of 271 g/mole, of which 22.9% (62 g/mole) is due to the two phosphorous atoms present in this molecule. One milligram of this compound is therefore calculated to have 0.229 mg P (1 mg×22.9%). Thus, to prepare a pharmaceutical composition containing 1.0 mg P of this compound, the composition should contain about 4.4 mg of the compound; to dose 1.0 mg P/kg of this compound to a 50 kg patient, the patient would be dosed with about 220 mg of this compound.

Similarly, the LED of the estrogen hormone is that level of the hormone which, by itself, is effective to prevent bone loss in subjects having osteoporosis. That level is generally recognized to be about 0.625 mg per day of conjugated estrogen or an equivalent dose of other estrogen hormones (for example, 25 µg per day of ethinyl estradiol; or 2 mg per day of 17-β-estradiol). See, Barzel, "Estrogens in the Prevention and Treatment of Post-Menopausal Osteoporosis: a Review", 85 *American Journal of Medicine* 847 (1988); Lindsay, et al., "The Minimum Effective Dose of Estrogen for Prevention of Post-Menopausal Bone Loss", 63 *Obstetrics and Gynecology* 759 (1984); Genant et al., "Effect of Estrone Sulfate on Postmenopausal Bone Loss", 76 *Obstetrics and Gynecology* 529 (1990); all of which are incorporated by reference herein.

The bone-active phosphonate and estrogen hormone may be administered concurrently or sequentially. Preferably, the estrogen hormone is administered daily, to provide a daily dose of from about 0.2 to about 0.8 LED. Medroxyprogesterone (and/or an equivalent hormone such as progesterone) may be administered concurrently, to mitigate potential side effects of the estrogen hormone. The estrogen hormone may also be administered in cyclical regimens. One such cyclical regimen comprises administering the estrogen hormone for one or more days, followed by a "free" period of one or more days in which the active is not administered, with repetition of the cycle. One such cyclical regimen for administering the estrogen hormone is administering the estrogen hormone for about 21 days, followed by a free period of about 7 days. Medroxyprogesterone may be administered during the free period. Another such cyclical regimen for administering the estrogen hormone comprises administering the estrogen hormone for about 14 days, followed by administrating the estrogen hormone together with medroxyprogesterone for about 11 days. Such regimens are generally described in Rudy, "Hormone Replacement Therapy—How to Select the Best Preparation and Regimen," 88 *Postgraduate Medicine* 157 (1990), incorporated by reference herein.

A preferred method of administering the bone-active phosphonate is daily, providing at least about 0.1 LED of active. Another preferred method of administering the bone-active phosphonate is in a cyclical regimen, comprising administering at least about 0.1 LED of active for one or more days, followed by one or more days where the bone-active phosphonate is not administered, with repetition of the cycle. Such cyclical regimens are generally described in U.S. Pat. No. 4,761,406, Flora et al., issued Aug. 2, 1988; U.S. Pat. No. 4,812,304, Anderson et al., issued Mar. 14, 1989; and U.S. Pat. No. 4,822,609, Flora, issued Apr. 18, 1989; all of which are incorporated by reference herein. A preferred method of this invention involves cyclical administration of 1-hydroxyethane-1,1-bisphosphonic acid, or a pharmaceutically-acceptable salt thereof, in cycles comprising administering the phosphonate for about 14 days, followed by a free period of about 76 days. During the free period, calcium nutritional supplements may be administered.

The methods of this invention comprise treatment of osteoporosis at all stages of the disorder. Since osteoporosis is an ongoing process of bone loss, rather than a disorder having a discrete beginning- or end-point, "treatment", as referred to herein, consists of any method which stops, slows, or reverses the process of bone loss which occurs in osteoporosis. Accordingly, a preferred method of this invention comprises treatment of a postmenopausal female subject before a significant loss of net skeletal mass has occurred in said subject. Such preferred methods are, in essence, methods of preventing osteoporosis. Preferably, such methods comprise treatment of said postmenopausal female subject beginning at the menopause in said subject. Such treatment preferably continues for at least five years.

Preferred methods of this invention also comprise treatment of osteoporosis in subjects who have already lost skeletal mass (herein referred to as "established osteoporosis"). Such methods of this invention for the treatment of established osteoporosis preferably comprise administering of the actives for a period of time sufficient to achieve an increase in the net skeletal mass of said subject. The increase in mass may be in cortical bone, trabecular bone, or both. Preferably, the net skeletal mass is increased by at least about 1%, more preferably at least about 5%.

The specific period of time sufficient to achieve an increase in the net skeletal mass of the subject may depend on a variety of factors. Such factors include, for example, the specific actives employed, the amount of actives administered, the age and sex of the subject, the specific disorder to be treated, concomitant therapies employed (if any), the general physical health of the subject (including the presence of other disorders), the extent of bone loss in the individual, and the nutritional habits of the individual.

The methods of this invention are preferably continued for at least about six months, preferably for at least about twelve months. Of course, such administration may be continued indefinitely, according to sound medical practice. Preferably the subject is treated until a net skeletal mass is obtained that is clinically determined to be above the fracture threshold for the subject. See, B. L. Riggs et al., "Involutional Osteoporosis" 314 *New England J. of Medicine* (1986), incorporated by reference herein.

In the methods of this invention, "administering" refers to any method which, in sound medical practice, delivers the actives used in this invention to the subject to be treated in such a manner so as to be effective in the building of bone. The actives may be administered by any of a variety of known methods of administration, e.g., orally, dermatomucosally (for example, dermally, sublingually, intranasally, and rectally), parenterally (for example, by subcutaneous injection, intramuscular injection, intra-articular injection, intravenous injection), and by inhalation. Thus, specific modes of administration include, for example, oral, transdermal, mucosal, sublingual, intramuscular, intravenous, intraperitoneal, subcutaneous administration, and topical application.

A preferred method for the treatment of osteoporosis includes an initial diagnostic step, to determine the presence of the disorder. Thus, a preferred method of this invention comprises the steps of performing a diagnostic on a human subject for the detection of osteoporosis and, upon obtaining a positive result from said diagnostic, administering the actives according to the methods of this invention. For such methods for treatment of postmenopausal female subjects prior to significant bone loss, said initial diagnostic step comprises performing a diagnostic for determining menopause. Such methods are well known in the art, and include determination of the bone mass and rate of bone remodeling. The rate of bone remodeling can be determined by measurement of biochemical markers. See, Hui et al., "The Contribution of Bone Loss to Postmenopausal Osteoporosis," 1 *Osteoporosis Int.* 30 (1990), incorporated by reference herein.

Suitable diagnostics for the detection of established osteoporosis are also well known in the art. Such methods include the measurement of the radiodensity of skeletal radiographs, quantitative computerized tomography, single energy photon absorptiometry, and dual-energy photon absorptiometry. Diagnostic techniques among those useful herein are described in W. A. Peck et al., Physician's Resource Manual on Osteoporosis (1987), published by the National Osteoporosis Foundation (incorporated by reference herein).

Dosage Forms:

The bone-active phosphonate and estrogen hormone may be administered in any of a variety of pharmaceutically-acceptable compositions. Such compositions may comprise an active and a pharmaceutically-acceptable carrier, or may comprise both actives and a pharmaceutically-acceptable carrier. Accordingly, compositions for coadministering both actives comprise:

(a) at least about 0.1 LED of a bone-active phosphonate;

(b) from about 0.2 to about 0.8 LED of an estrogen hormone; and (c) a pharmaceutically-acceptable carrier.

Pharmaceutically-acceptable carriers include solid or liquid filler diluents or encapsulating substances, and mixtures thereof, that are suitable for administration to a human or lower animal. The term "compatible", as used herein, means that the components of the pharmaceutical composition are capable of being commingled with the actives, and with each other, in a manner such that there is no interaction which would substantially reduce the pharmaceutical efficacy of the pharmaceutical composition under ordinary use situations. Pharmaceutically-acceptable carriers must, of course, be of sufficiently high purity and sufficiently low toxicity to render them suitable for administration to the human or lower animal being treated.

Some examples of the substances which can serve as pharmaceutical carriers are: sugars, such as lactose, glucose and sucrose; starches, such as corn starch and potato starch; cellulose and its derivatives, such as sodium carboxymethylcellulose, ethylcellulose, cellulose acetate; powdered tragacanth; malt; gelatin; talc; stearic acid; magnesium stearate; vegetable oils, such as peanut oil, cottonseed oil, sesame oil, olive oil, corn oil and oil of theobroma; polyols such as propylene glycol, glycerin, sorbitol, mannitol, and polyethylene glycol; agar; alginic acid; pyrogen-free water; isotonic saline; phosphate buffer solutions; wetting agents and lubricants such as sodium lauryl sulfate; coloring agents; flavoring agents; and preservatives. Other compatible pharmaceutical additives and actives may be included in the pharmaceutically-acceptable carrier for use in the compositions of the present invention.

The choice of a pharmaceutically-acceptable carrier to be used in conjunction with the active is determined by the way the active is to be administered. If the active is to be injected, the preferred pharmaceutical carrier is sterile water, physiological saline, or mixtures thereof. The pH of such parenteral composition is preferably adjusted to about 7.4. Suitable pharmaceutically-acceptable carriers for topical application include those known in the art for use in creams, gels, tapes, patches, and similar topical delivery means.

The pharmaceutically-acceptable carrier employed in conjunction with the actives is used at a concentration sufficient to provide a practical size to dosage relationship. The pharmaceutically-acceptable carriers, in total, may comprise from about 0.1% to about 99.9% by weight of the pharmaceutical compositions of the present invention, preferably from about 5% to about 80%, and most preferably from about 10% to about 50%.

A preferred method of administering actives is orally, in a unit-dosage form (i.e., a dosage form containing an amount of active suitable for administration in one single dose, according to sound medical practice). Preferred unit dosage forms include tablets, capsules, suspensions, and solutions, comprising a safe and effective amount of active. Pharmaceutically-acceptable carriers suitable for the preparation of unit dosage forms for oral administration are well known in the art. Their selection will depend on secondary considerations like taste, cost, shelf stability, which are not critical for the purposes of the present invention, and can be made without difficulty by a person skilled in the art. Preferably, oral unit dosage forms of the bone-active phosphonate comprise from about 1 mg P to about 600 mg P of the phosphonate.

Kits:

This invention also provides kits for conveniently and effectively implementing the methods of this invention. Such kits comprise one or more unit doses of bone-active phosphonate, one or more unit doses of estrogen hormone, and a means for facilitating compliance with methods of this invention. Such kits provide a convenient and effective means for assuring that the subject to be treated takes the appropriate active in the correct dosage in the correct manner. Such kits are particularly preferred in methods of this invention which employ cyclical regimens for administration of either, or both, actives.

The compliance means of such kits includes any means which facilitates administering the actives according to a method of this invention. Such compliance means includes instructions, packaging, and dispensing means, and combinations thereof. Examples of packaging and dispensing means are well known in the art, including those described in U.S. Pat. No. 4,761,406, Flora et al., issued Aug. 2, 1988; and U.S. Pat. No. 4,812,311, Uchtman, issued Mar. 14, 1989, both of which are incorporated by reference herein.

The following non-limiting examples illustrate the compositions, processes and uses of the present invention.

EXAMPLE 1

A human female subject weighing about 60 kg (132 lbs), suffering from postmenopausal osteoporosis, is treated by a method of this invention. Specifically, for two years:
(1) disodium 1-hydroxyethane-1,1-bisphosphonate is administered, in a cyclic regimen, where each cycle consists of orally administering a tablet[1] containing 200mg of the phosphonate each day for 14 days, followed by a 76-day free period during which no bone-active phosphonate is administered; and
(2) conjugated estrogen is administered, by daily administering a tablet[2] containing 0.3 mg of active.

In this regimen, the bone-active phosphonate is administered at a level of about 0.5 LED, and estrogen hormone is administered at a level of about 0.5 LED. The density of the subject's vertebrae is then measured by dual-energy photon absorptiometry, indicating an increase in bone mass.

1: sold by Norwich Eaton Pharmaceuticals, Inc., under the trademark "Didronel", in tablets containing 200 mg of active in a carrier of magnesium stearate, microcyrstalline cellulose and starch 2: sold by Wyeth-Ayerst Laboratories, under the trademark "Premarin", in a carrier of calcium phosphonate tribasic, calcium sulfate anhydrous, caruauba wax, glyceryl monooleate, lactose, magnesium stearate, methylcellulose, microcrystalline cellulose, polyethylene glycol, stearic acid, sucrose, talc and titanium dioxide

EXAMPLE 2

A human female subject weighing about 60 kg (132 lbs), suffering from postmenopausal osteoporosis, is treated by a method of this invention. Specifically, for one year:
(1) 2-(3-pyridyl)-1-hydroxyethane-1,1-bisphosphonic acid is administered, daily, in a tablet containing 15 mg of active; and
(2) 17-β-estradiol is administered daily, from a transdermal patch delivering 0.03 mg active per day.

In this regimen, the bone-active phosphonate is administered at a level of about 1.0 LED, and estrogen hormone is administered at a level of about 0.5 LED. The density of the subject's vertebrae is then measured by dual-energy photon absorptiometry, indicating an increase in bone mass. In this example, the following bone active phosphonates: dichloro methane bisphosphonic acid, 3-amino-1-hydroxypropane-1,1-bisphosphonic acid, 4-amino-1-hydroxybutane-1,1-bisphosphonic acid, 6-amino-1-hydroxyhexane-1,1-bisphosphonic acid; N-(2-pyridyl) aminomethane-1,1-bisphosphonic acid; 2-(2-pyridyl)-1-hydroxy ethane-1-phosphono-1-methylphosphinic acid; 2-(3-pyridyl)-1-hydroxyethane-1-phosphono-1-methylphosphinic acid; 2-(N-imidazoyl)-1-hydroxyethane-1-phosphono-1-methylphosphinic acid; 3-(N-pentyl-N-methylamino)-1-hydroxypropane-1-phosphono-1-methyl phosphinic acid; 4-amino-1-hydroxybutane-1-phosphono-1-methylphosphinic acid; 3-(N-pyrol-lidino)-1-hydroxypropane-1-phosphono-1-methylphosphinic acid; N-cycloheptylaminomethanephosphonomethyl phosphinic acid; S-(p-chlorophenyl) thiomethanephosphonomethylphosphinic acid; (7-dihydro-1-pyrindine)methanephosphonomethylphosphinic acid; (7-dihydro-1-pyrindine)hydroxymethanephosphonomethyl phosphinic acid; (6-dihydro-2-pyrindine) hydroxymethanephosphonomethylphosphinic acid; 2-(6-pyrolopyridine)-1-hydroxyethane-1-phosphono-1-methylphosphinic acid; 2-(3-pyridyl)-1-hydroxy ethane-1,1-bisphosphonic acid; 2-(N-imidazoyl)-1-hydroxyethane-1,1-bisphosphonic acid; 3-(N-pentyl-N-methylamino)-1-hydroxypropane-1,1-bisphosphonic acid; 3-(N-pyrollidino)-1-hydroxypropane-1,1-bisphosphonic acid; N-cycloheptylaminomethanebisphosphonic acid; S-(p-chlorophenyl)thiomethanebisphosphonic acid; (7-dihydro-1-pyrindine) methanebisphosphonic acid; (7-dihydro-1-pyrindine)hydroxymethane bisphosphonic acid; (6-dihydro-2-pyrindine)hydroxymethanebisphosphonic acid; 2-(6-pyrolopyridine)-1-hydroxyethane-1,1-bisphosphonic acid; are substituted for 2-(2-pyridyl)-1-hydroxyethane-1,1-bisphosphonic acid, at comparable levels, with substantially similar results.

EXAMPLE 3

A human female subject weighing about 60 kg (132 lbs) is evaluated approximately six months after spontaneous menopause, and is found to have low bone mass and an abnormally high rate of bone remodeling. The subject is then treated by a method of this invention to prevent osteoporosis. Specifically, each day for five years, the subject is administered a tablet comprised as follows.

| Component | milligrams/tablet |
| --- | --- |
| 2-(2'piperidinyl)-ethane-1-phosphono-1-methylphosphinic acid | 120 |
| conjugated estrogen | 0.5 |
| lactose | 80 |
| microcrystalline cellulose | 50 |
| sodium starch glycolate | 7.5 |
| magnesium stearate | 1.5 |

Each tablet contains about 0.3 LED bone-active phosphonate, and about 0.8 LED estrogen hormone. The density of the subject's vertebrae is then measured, indicating that no significant loss in bone mass has occurred.

What is claimed is:

1. A method of treatment for osteoporosis in a human or other animal subject, comprising: administering a bone-active phosphonate to said subject, at a level of at least about 0.1 LED per day of said treatment; and and administering an estrogen hormone to said subject, at a level of from about 0.2 to about 0.8 LED per day of said treatment.

2. A method of treatment for osteoporosis, according to claim 1, wherein said bone-active phosphonate is administered at a level of from about 0.2 to about 1.0 LED per day of said treatment.

3. A method of treatment for osteoporosis, according to claim 2, of a postmenopausal female subject before a significant loss of net skeletal mass has occurred in said subject.

4. A method of treatment for osteoporosis, according to claim 2, wherein said bone-active phosphonate is administered in a cyclical regimen.

5. A method of treatment for osteoporosis, according to claim 2, wherein said estrogen hormone is administered at level of about 0.5 LED per day of said treatment.

6. A method of treatment for osteoporosis, according to claim 1, wherein said bone-active phosphonate is a bisphosphonic acid, or a pharmaceutically-acceptable salt or ester thereof.

7. A method of treatment for osteoporosis, according to claim 6, wherein said bisphosphonic acid is of the formula:

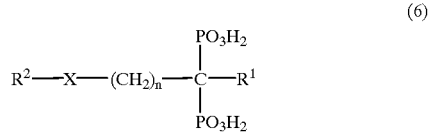

(6)

wherein: n is an integer from 0 to 7; $R^1$ is hydrogen, chloro, amino, or hydroxy; X is —NH—, oxygen, or a single bond; $R^2$ is a 5- to 7-membered heterocycle having from 1 to 3 heteroatoms, amino, amino substituted with one or two lower alkyl groups, or hydrogen; and their pharmaceutically-acceptable salts and esters.

8. A method of treatment for osteoporosis, according to claim 6, wherein said bisphosphonic acid is selected from the group consisting of: 1-hydroxyethane-1,1-bisphosphonic acid; dichloromethane bisphosphonic acid; 3-amino-1-hydroxypropane-1,1-bisphosphonic acid; 6-amino-1-hydroxyhexane-1,1-bisphosphonic acid; 4-amino-1-hydroxybutane-1,1-bisphosphonic acid; 2-(3-pyridyl)-1-hydroxyethane-1,1-bisphosphonic acid; 2-(N-imidazoyl)-1-hydroxyethane-1,1-bisphosphonic acid; 3-(N-pentyl-N-methylamino)-1-hydroxypropane-1,1-bisphosphonic acid; 3-(N-pyrollidino)-1-hydroxypropane-1,1-bisphosphonic acid; N-cycloheptylaminomethanebisphosphonic acid; S-(p-chlorophenyl)thiomethanebisphosphonic acid; (7-dihydro-1-pyrindine)methanebisphosphonic acid; (7-dihydro-1-pyrindine)hydroxymethanebisphosphonic acid; (6-dihydro-2-pyrindine)hydroxymethanebisphosphonic acid; 2-(6-pyrolopyridine)-1-hydroxyethane-1,1-bisphosphonic acid; 2-(2-pyridyl)-1-hydroxy-ethane-1,1-bisphosphonic acid; and pharmaceutically-acceptable salts and esters thereof.

9. A method of treatment for osteoporosis, according to claim 8, wherein said bisphosphonic acid is 2-(3-pyridyl)-1-hydroxyethane-1,1-bisphosphonic acid, or a pharmaceutically acceptable salt or ester thereof.

10. A method of treatment for osteoporosis, according to claim 1, wherein said estrogen hormone is selected from the group consisting of estradiol, estrone, estriol, equilin, equilenin, estradiol cypionate, estradiol valerate, ethyinyl estradiol, polyestradiol phosphate, estropipate, diethylstilbestrol, dienestrol, chlorotrianisene, and mixtures thereof.

11. A unit dosage form composition, for the treatment of osteoporosis, comprising:

(a) at least about 0.1 LED of a bone-active phosphonate;

(b) from about 0.2 to about 0.8 LED of an estrogen hormone; and (c) a pharmaceutically-acceptable carrier.

12. A method of treatment for osteoporosis in a human or other animal subject, comprising administering to said subject one unit dosage form of claim 11 per day of said treatment.

13. A method of treatment according to claim 9, wherein said estrogen hormone is estradiol.

14. A unit dosage form composition, according to claim 11, wherein said bone-active phosphonate is 2-(3-pyridyl)-1-hydroxyethane-1,1-bisphosphonic acid, or a pharmaceutically-acceptable salt or ester thereof.

15. A unit dosage form composition according to claim 14, wherein said estrogen hormone is estradiol.

16. A method of treatment for osteoporosis in a human or other animal subject, comprising administering to said subject one unit dosage form of claim 14 per day of said treatment.

17. A method of treatment for osteoporosis in a human or other animal subject, comprising administering to said subject one unit dosage form of claim 15 per day of said treatment.

* * * * *